(12) United States Patent
Grove et al.

(10) Patent No.: US 8,188,123 B2
(45) Date of Patent: May 29, 2012

(54) (PYRROLIDIN-2-YL)PHENYL DERIVATIVES

(76) Inventors: Simon James Anthony Grove, Newhouse (GB); Ronald Palin, Newhouse (GB); Ashvinkumar Dhirubhai Mistry, Newhouse (GB); John Kinnaird Ferguson MacLean, Newhouse (GB)

( * ) Notice: Subject to any disclaimer, the term of this patent is extended or adjusted under 35 U.S.C. 154(b) by 277 days.

(21) Appl. No.: 12/611,468

(22) Filed: Nov. 3, 2009

(65) Prior Publication Data
US 2010/0113493 A1 May 6, 2010

Related U.S. Application Data

(60) Provisional application No. 61/111,070, filed on Nov. 4, 2008.

(51) Int. Cl.
*A61K 31/4439* (2006.01)
*C07D 401/10* (2006.01)
(52) U.S. Cl. ..................... 514/343; 546/276.4
(58) Field of Classification Search .............. 514/343; 546/276.4
See application file for complete search history.

(56) References Cited

U.S. PATENT DOCUMENTS
6,339,099 B1 * 1/2002 Lam et al. ..................... 514/378
* cited by examiner

*Primary Examiner* — Patricia Morris
(74) *Attorney, Agent, or Firm* — Susan L. Hess; Gerard M. Devlin

(57) ABSTRACT

The invention relates to (pyrrolidin-2-yl)phenyl derivatives having the general Formula I

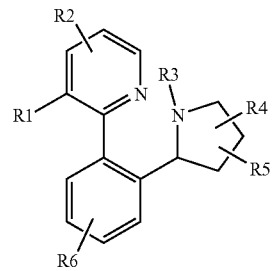

Formula I wherein $R_1$ is $(C_{1-4})$alkyl, halo$(C_{1-4})$alkyl, $(C_{1-4})$alkyloxy, or halo$(C_{1-4})$alkyloxy; $R_2$ is H, $(C_{1-4})$alkyl, halo$(C_{1-4})$alkyl, $(C_{1-4})$alkyloxy, halo$(C_{1-4})$alkyloxy or halogen; $R_3$ is H, $(C_{1-4})$alkyl or halo$(C_{1-4})$alkyl; $R_4$ is H, $(C_{1-4})$alkyl or halo$(C_{1-4})$alkyl; $R_5$ is H, $(C_{1-4})$alkyl or halo-$(C_{1-4})$-alkyl; or $R_4$ and $R_5$, when bonded to the same carbon atom, can together with the carbon atom form a spiro$(C_{3-6})$cycloalkyl group, optionally substituted with halogen; $R_6$ is H, $(C_{1-4})$alkyl, halo$(C_{1-4})$alkyl, $(C_{1-4})$alkyloxy, halo$(C_{1-4})$alkyloxy or halogen; or a pharmaceutically acceptable salt thereof, to pharmaceutical compositions comprising the same, as well as to the use of these (pyrrolidin-2-yl)phenyl derivatives for the treatment of pain, such as neuropathic pain or inflammatory pain.

23 Claims, No Drawings

(PYRROLIDIN-2-YL)PHENYL DERIVATIVES

This application is a non-provisional application that claims priority under 35 U.S.C. §119(e) of provisional application U.S. Ser. No. 61/111,070 filed Nov. 4, 2008, the contents of which are hereby incorporated by reference in their entirety.

This invention relates to (pyrrolidin-2-yl)phenyl derivatives, to pharmaceutical compositions comprising the same and to the use of these (pyrrolidin-2-yl)phenyl derivatives in the treatment of chronic neuropathic pain.

Neuropathic pain, or the spontaneous pain and abnormal sensitivity following a nerve injury, typically results from a traumatic injury, an infection or disease, or surgery, and can persist long after the initial injury has healed. Current treatment options are limited or inadequate for many people.

HCN channels are the molecular substrates of the currents known as $I_h$, $I_f$ or $I_q$. Hyperpolarization-activated, cyclic nucleotide-gated (HCN) channels, also known as pacemaker channels, first identified in cardiac pacemaker cells (Di Francesco, 1993 Annu Rev Physiol. 55:455-472), have also been found in a variety of peripheral and central neurones (e.g. Notomi & Shigemoto 2004 J. Comp. Neurol. 471: 241-276). These channels are slowly activated by hyperpolarization to generate depolarizing inward current (termed $I_f$ in cardiac cells and $I_h$ in neurones) and are permeable to both sodium and potassium ions. The four HCN channel isoforms are present in pain-processing regions of the nervous system including thalamus, amygdala, spinal cord & primary sensory neurones. It is likely that all four subunits are present in dorsal root ganglia (DRG), with HCN1 having the highest level of expression, this is consistent with the activation kinetics of $I_h$ current recorded from DRG (Tu et al., J Neurosci. Res. 2004 76:713-722).

$I_h$ current has been detected in neurons from many regions of the nervous system involved in nociception, including the substantia gelatinosa of spinal cord, dorsal root ganglia, amygdala, cingulate cortex and the thalamus. $I_h$ currents appear to be preferentially expressed by medium/large DRGs and may be absent from the somata of most C-type (small) DRGs (Scroggs et al., J Neurophysiol. 71: 271-279; Tu et al., J Neurosci. Res. 2004 76:713-722). Furthermore, it has been reported that nerve injury in rats (Chung model) increased $I_h$ current density in large DRGs and caused pacemaker-driven, spontaneous action potentials in the ligated nerve. ZD 7288, an $I_h$ channel blocker, reduced the firing frequency of ectopic discharges in A-beta and A-delta fibres, without causing conduction block (Lee et al 2005 J Pain 417-424).

Intraperitoneal administration of an $I_h$ blocker, ZD 7288, in a model of neuropathic pain, dose-dependently reverses mechanical allodynia (Chung/von Frey; Chaplan, et al 2003 J Neurosci. 23: 1169-1178). ZD 7288 also suppresses allodynia in the rat CFA model of inflammatory pain and blocks spontaneous pain in a rat, mild thermal injury model. Another research group has reported that local administration of ZD 7288 to the sciatic nerve 4 h after surgery in rats attenuates mechanical allodynia in the Brennan model (Dalle & Eisenach 2005 Reg. Anesth. and Pain Med 243-248).

It is hypothesised that, during chronic painful conditions, primary afferents become hyperexcitable due to peripheral sensitisation after inflammation, and a change of ion channel expression at the site of nerve damage associated with neuropathy. ZD 7288-induced inhibition of $I_h$ reduces spontaneous activity in nerve injured myelinated DRG (Yagi et al, 2000 Proc 9th World Congress on Pain 109-117) so reducing the associated pain. Current preclinical data indicate that $I_h$ channel blockers will have utility in the treatment of chronic neuropathic pain.

A need thus exists for compounds that are useful in the treatment of pain states mediated by the $I_h$-channel.

To this end the present invention provides (pyrrolidin-2-yl) phenyl derivatives having the general Formula I

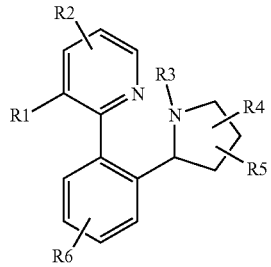

Formula I wherein
R$_1$ is (C$_{1-4}$)alkyl, halo(C$_{1-4}$)alkyl, (C$_{1-4}$)alkyloxy, or halo(C$_{1-4}$)alkyloxy;
R$_2$ is H, (C$_{1-4}$)alkyl, halo(C$_{1-4}$)alkyl, (C$_{1-4}$)alkyloxy, halo(C$_{1-4}$)alkyloxy or halogen;
R$_3$ is H, (C$_{1-4}$)alkyl or halo(C$_{1-4}$)alkyl;
R$_4$ is H, (C$_{1-4}$)alkyl or halo(C$_{1-4}$)alkyl;
R$_5$ is H, (C$_{1-4}$)alkyl or halo(C$_{1-4}$)alkyl; or
R$_4$ and R$_5$, when bonded to the same carbon atom, can together with the carbon atom form a spiro(C$_{3-6}$)cycloalkyl group, optionally substituted with halogen;
R$_6$ is H, (C$_{1-4}$)alkyl, halo(C$_{1-4}$)alkyl, (C$_{1-4}$)alkyloxy, halo(C$_{1-4}$)alkyloxy or halogen; or
a pharmaceutically acceptable salt thereof.

The term (C$_{1-4}$)alkyl as used in the definition of Formula I means a branched or unbranched alkyl group having 1-4 carbon atoms, like butyl, isobutyl, tertiary butyl, propyl, isopropyl, ethyl and methyl.

The term halo(C$_{1-4}$)alkyl means a (C$_{1-4}$)alkyl group which is substituted with 1 or more halogens. A preferred halo(C$_{1-4}$)alkyl group is trifluoromethyl.

In the terms (C$_{1-4}$)alkyloxy and halo(C$_{1-4}$)alkyloxy, (C$_{1-4}$) alkyl and halo(C$_{1-4}$)alkyl have the meanings as described above.

The term halogen means F, Cl, Br or I. A preferred halogen is F.

There is a preference for (pyrrolidin-2-yl)phenyl derivatives according to Formula I, wherein R$_1$ is halo(C$_{1-4}$)alkyl, especially trifluoromethyl.

Further preferred are the compounds according to Formula I wherein R$_2$, R$_3$, R$_4$ and R$_5$ are H and R$_6$ is H or F.

The S-stereoisomers of the (pyrrolidin-2-yl)phenyl derivatives according to Formula I are preferred.

Specifically preferred (pyrrolidin-2-yl)phenyl derivatives of the invention are:
2-(2-((S)-pyrrolidin-2-yl)phenyl)-3-(trifluoromethyl)pyridine;
2-(2-((R)-pyrrolidin-2-yl)phenyl)-3-(trifluoromethyl)pyridine;
2-(5-fluoro-2-(pyrrolidin-2-yl)phenyl)-3-(trifluoromethyl) pyridine;
6-(2-(3-(trifluoromethyl)pyridin-2-yl)phenyl)-5-azaspiro [2.4]heptane;
2-(5-methyl-2-(pyrrolidin-2-yl)phenyl)-3-(trifluoromethyl) pyridine;
2-(2-(pyrrolidin-2-yl)phenyl)-3-methylpyridine;

2-(4-fluoro-2-(pyrrolidin-2-yl)phenyl)-3-methylpyridine;

2-(5-fluoro-2-(pyrrolidin-2-yl)phenyl)-3-methylpyridine;

2-(2-(pyrrolidin-2-yl)phenyl)-3-methoxypyridine;

2-(4-fluoro-2-(pyrrolidin-2-yl)phenyl)-3-methoxypyridine;

2-(5-fluoro-2-(pyrrolidin-2-yl)phenyl)-3-methoxypyridine;
or a pharmaceutically acceptable salt thereof.

The (pyrrolidin-2-yl)phenyl derivatives of the invention may be prepared by methods known in the art of organic chemistry in general.

Compounds of Formula 1 where $R_3$ is $C_{(1-4)}$ alkyl can be prepared from compounds of Formula 1 where $R_3$ is H by alkylating with reagents of Formula $R_3X$, wherein $R_3$ has the meaning as previously given, and wherein X represents a leaving group such as chloro, bromo, iodo or an aryl or alkyl sulphonate, such as a tosylate or mesylate, in a solvent such as N,N-dimethylformamide or acetonitrile and using a basic reagent such as triethylamine, diisopropylethylamine or sodium carbonate. Compounds of Formula 1 where $R_3$ is $C_{(1-4)}$ alkyl can also be prepared by treatment of a compound of formula I wherein $R_3$ is H with a $C_{(1-4)}$ aldehyde or ketone in the presence of a reducing agent such as formic acid, formamide or a metal hydride reagent such as sodium borohydride, sodium triacetoxyborohydride, sodium cyanoborohydride or lithium aluminium hydride at a temperature preferably between 0° C. and 100° C.

Compounds of Formula 1 where $R_3$ is H can be prepared by deprotecting compounds of Formula 2, wherein $R_1$, $R_2$, $R_4$, $R_5$ and $R_6$ have the meaning as previously defined and wherein PG is a protecting group such as a tert-butoxycarbonyl (BOC), benzyloxy-carbonyl (CBZ) or trichloroethoxycarbonyl (TROC). Such deprotection steps are well known to those skilled in the art. Methods described in Greene T. W. 'Protecting Groups in Organic Synthesis' New York, Wiley (1981) may be used.

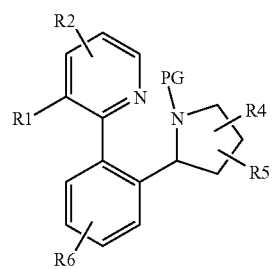

Formula 2

Compounds of Formula 2 can be prepared from compounds of Formula 3 where X' is a halogen, preferably bromo or iodo, or a sulfonate such as a trifluoromethanesulfonate (triflate) and a reagent of Formula 4 where M is a metallic species such as a boronic acid, a boronate ester such as pinicolatoborate or neopentyl glycolatoboranane. Such a cross coupling reaction is performed in the presence of a transition metal catalyst, preferably a palladium catalyst such as tetrakis (triphenylphoshine)palladium (0) or palladium (II) acetate, in the presence of a base such as sodium carbonate in a solvent such as toluene, N,N-dimethylformamide or 1,2-dimethoxyethane at an elevated temperature, preferably greater than 100° C. The reaction may also be conducted by heating using microwave irradiation as heat source.

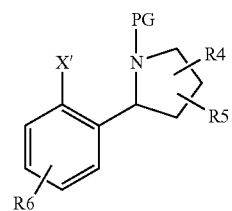

Formula 3

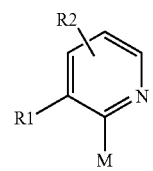

Formula 4

Compounds of Formula 4 can be prepared from compounds of Formula 6 by methods known to those skilled in the art.

Alternatively compounds of Formula 2 can be prepared from compounds of Formula 5 and Formula 6 where X' and M have the same definitions as described above, using the same cross coupling conditions to those described above for coupling compounds of Formula 3 and Formula 4.

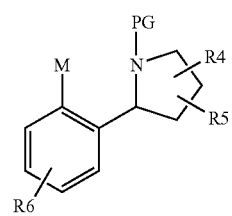

Formula 5

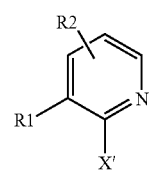

Formula 6

Compounds of Formula 5 can be prepared from compounds of Formula 3 by methods known to those skilled in the art. Such methods include lithium-halogen exchange followed by transmetallation with a reagent such as zinc chloride, quenching the lithium species with a borate reagent such as triisopropyl borate followed by hydrolysis to give the boronic acid or with a stannane reagent such as tri-n-butyl tin chloride. Compounds of Formula 5 where M is a borate ester may be prepared from compounds of Formula 3 and an appropriate diborane species including but not limited to bis(pinacolato)borane or bis(neopentyl glycolato)diborane [5,5,5',5'-tetramethyl-2,2'-bi(1,3,2-dioxaborinane)] in the presence of a transition metal catalyst such as 1,1'-bis(diphenylphospino) ferrocene-dichloropalladium (II) and a ligand such as 2-dicyclohexylphosphino-2',6'-di-iso-propoxy-1,1'-biphenyl in a solvent such as dimethyl sulfoxide at an elevated temperature.

Compounds of Formula 3 may be prepared from compounds of Formula 7 by protection methods well known to persons skilled in the art. Methods described in Greene T. W. 'Protecting Groups in Organic Synthesis' New York, Wiley (1981) may be used. An example of such a protecting group (PG) is the tert-butyloxycarbonyl group. This transformation is readily achieved using compounds of Formula 7 and di-tert-butyl dicarbonate in a solvent such as tetrahydrofuran at ambient temperature.

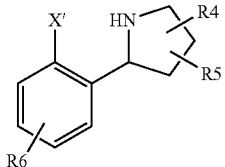

Formula 7

Compounds of Formula 7 may be prepared from compounds of Formula 8 by reduction with a suitable reducing agent such as sodium borohydride in a solvent such as tetrahydrofuran at ambient temperature.

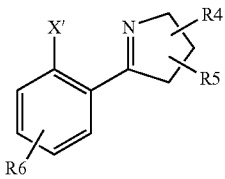

Formula 8

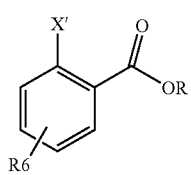

Formula 9

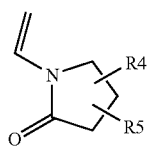

Formula 10

Compounds of Formula 8 where $R_4$ and $R_5$ are H can be prepared from compounds of Formula 9 where R is an alkyl group by treatment with an N-vinylpyrrolidinone reagent of Formula 10 in presence of a base such as sodium hydride followed by acid hydrolysis of the initial intermediate formed and basic work up. This method of pyrrolidine synthesis has been described in the literature (B. E. Maryanoff et al, *J. Med. Chem.*, 1987, 30, 1433 and P. Jacob III, *J. Org. Chem.*, 1982, 47, 4165).

Compounds of Formula 7 may be prepared from compounds of Formula 11 where Ar is an aryl ring preferably phenyl or phenyl optionally substituted with halogens by treatment with a base such as potassium tert-butoxide in a solvent such as tetrahydrofuran at a temperature between −78° C. and ambient temperature followed by the addition of a reagent of Formula 12 where the X is defined as before and X" is a halogen or a sulfonate such as a tosylate group, X can be the same as X" in Formula 11. After the addition of the base and addition of a compound of Formula 12 the reaction is acidified then neutralised and basified.

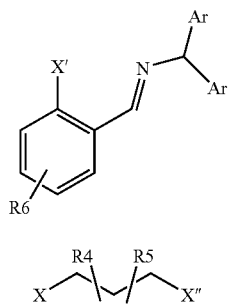

Formula 11

Formula 12

Compounds of Formula 7 may be prepared from compounds of Formula 13 by deprotection (i.e. removal of PG, by deprotection methods well known to persons skilled in the art) and basification giving concomitant cyclisation. Compounds of Formula 13 can be made by treatment of a compound of Formula 14 with an aryl or alkyl sulfonyl halide of general formula $RSO_2Hal$ in a solvent such as methylene chloride in the presence of a base such as triethylamine. Compounds of Formula 14 can be prepared from compounds of Formula 15 by means of a hydroboration-oxidation sequence such as treatment with 9-borabicyclo[3.3.1]nonane (9-BBN) or thexylborane followed by buffered hydrogen peroxide. A compound of general Formula 15 where PG has the definition described above can be prepared from a compound of Formula 16 by a protection sequence as described above for the formation of compounds of Formula 3.

Formula 13

Formula 14

Formula 15

Formula 16

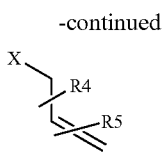

Formula 17

Compounds of Formula 16 can be prepared from compounds of Formula 11 by treatment with a base such as potassium tert-butoxide and reaction with an alkylating agent of general Formula 17 followed by acidic hydrolysis. A compound of general Formula 16 can also be made in optically pure form using methods in the literature known to those skilled in the art. Such methods include the removal of the chiral auxiliary from compounds of Formula 18 where CA is a chiral auxiliary. Compounds of Formula 18 can be prepared by the addition of allyl metal, of Formula 20 where M' is a metallic species preferably magnesium, lithium, indium or zinc, to an imine of Formula 19. An imine of Formula 19 can be prepared from an aldehyde of Formula 21 by treatment with an amine of formula CA-NH$_2$ and a dehydrating agent such a magnesium sulphate, titanium tetraethoxide, titanium tetrachloride or sodium sulfate. Such imine formations are known to those skilled in the art.

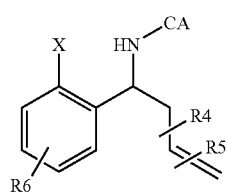

Formula 18

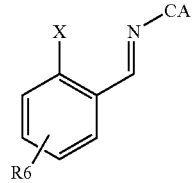

Formula 19

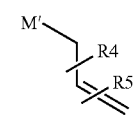

Formula 20

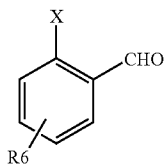

Formula 21

Examples of imines of Formula 19 include, but are not limited to, those imines derived from amine where CA-NH$_2$ is phenyl glycinamide (J. Dalmolen et al, *Eur. J. Org. Chem.* 2004, 1544 and M. vd Sluis et al, *Org Lett.*, 2001, 3, 3943), valine methyl ester or valinol (A. Bacoum et al, *J. Chem. Soc., Chem Commun.*, 1993, 1542) and phenyl glycinol (T. Valaivan, *J. Org. Chem.*, 2005, 70, 3464). Further examples of imines of Formula 19 include sulphinamines where CA is S(O)C$_6$H$_5$CH$_3$ or S(O)tBu with either stereochemistry at the sulphur centre. Imines of Formula 17 where CA is S(O)C$_6$H$_5$CH$_3$ or S(O)tBu with either stereochemistry at the sulphur centre may be prepared using the method described by P. Zhou et al, *Tetrahedron*, 2004, 60, 8003.

Compounds of Formula 7 where R$_4$ and R$_5$ are H may also be prepared from compounds of Formula 19 where CA is S(O)C$_6$H$_5$CH$_3$ or S(O)tBu with either stereochemistry at the sulphur centre following the method reported by K. M. Brinner and J. A. Ellman, *Org. Biomol. Chem.*, 2005, 3, 2109.

Other methods to generate a chiral compound for Formula 15 where R$_4$ and R$_5$ are H include the enantioselective transfer aminoallylation reaction (M. Sagiura et al, *J. Am. Chem. Soc.*, 2006, 128, 11038) starting from aldehydes of Formula 21.

The (pyrrolidin-2-yl)phenyl derivatives of Formula I and their salts may contain at least one centre of chirality, and exist therefore as stereoisomers, including enantiomers and diastereomers. The present invention includes the aforementioned stereoisomers within its scope and each of the individual R and S enantiomers of the compounds of Formula I and their salts, substantially free base, i.e. associated with less than 5%, preferably less than 2%, in particular less than 1% of the other enantiomer, and mixtures of such enantiomers in any proportions including the racemic mixtures containing substantially equal amounts of the two enantiomers.

Compounds of Formula 1, 2, 3, 5, 7, 13, 14, 15 and 16 can be resolved into single enantiomers using methods such as cystallisation of chiral salt forms, chiral chromatographic resolution or resolution using enzymatic methods. Such methods are well known to those skilled in the art. Methods described in '*Advanced Organic Chemistry*' (March J., New York, Wiley (1985) and in "*Chirality in Industry*" (Edited by A. N. Collins, G. N. Sheldrake and J. Cosby, 1992; John Wiley) may be used. Compounds of Formula 18 can be isolated as single diastereomers by using methods such as cystallisation or chromatographic resolution.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, fluorine and chlorine, such as $^2$H, $^3$H, $^{13}$C, $^{14}$C, $^{15}$N, $^{18}$O, $^{17}$O, $^{18}$F, and $^{36}$Cl, respectively.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed above and/or in the Examples hereinbelow, by substituting an appropriate isotopically labelled reagent for a non-isotopically labelled reagent.

Pharmaceutically acceptable salts may be obtained by treating a free base of a compound of Formula I with a mineral acid such as hydrochloric acid, hydrobromic acid, phosphoric acid and sulfuric acid, or an organic acid such as for example ascorbic acid, citric acid, tartaric acid, lactic acid, maleic acid, malonic acid, fumaric acid, glycolic acid, succinic acid, propionic acid, acetic acid and methane sulfonic acid.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a (pyrrolidin-2-yl)phenyl derivative according to general Formula I, or a pharmaceutically acceptable salt thereof, in admixture with one or more pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, ocular or rectal administration, and the like, all in unit dosage forms for administration. A preferred route of administration is the oral route.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al, Remington: *The Science and Practice of Pharmacy* (20th Edition, Lippincott Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as described before, in combination with packaging material suitable for said composition, said packaging material including instructions for the use of the composition for the use as described before.

The (pyrrolidin-2-yl)phenyl derivatives of the invention were found to be inhibitors of the Ih channel as measured by patch clamp electrophysiology using the human HCN1 channel (see international patent application WO 01/090142: "Full length human HCN1 $I_h$ channel subunits and variants"—Akzo Nobel N.V.) expressed in HEK cells.

The compounds of the invention have utility in the treatment of pain which is mediated through modulation of the $I_h$ channel, preferably neuropathic or inflammatory pain, such as neuropathic pain occurring in conditions like trigeminal neuralgia, post herpetic neuralgia (pain following shingles), diabetic neuropathy, phantom limb pain following amputation, multiple sclerosis, pain following chemotherapy, fibromyalgia (chronic muscle pain disorder), HIV infection, alcoholism, cancer (as a direct result of cancer on peripheral nerves or as a side effect of some chemotherapy drugs) and atypical facial pain.

The compounds of the invention could also be used in conjunction with other drugs, for example analgesic drugs such as opioids and non-steroidal anti-inflammatory drugs (NSAIDs), including COX-2 selective inhibitors.

The compounds of the invention may be administered to humans in a sufficient amount and for a sufficient amount of time to alleviate the symptoms. Illustratively, dosage levels for humans can be in the range of 0.001-50 mg per kg body weight, preferably in a dosage of 0.01-20 mg per kg body weight.

EXPERIMENTAL

Compound 1

(S,E)-2-(2-Bromobenzylideneamino)-2-phenylethanol

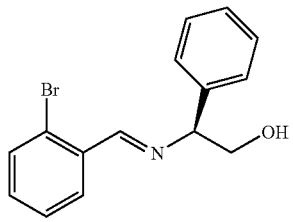

To a stirred solution of (S)-(+)-2-amino-2-phenylethanol (271 mmol, 37.2 g) in methylene chloride (350 mL) was added 2-bromobenzaldehyde (271 mmol, 31.8 mL, 50.2 g) and anhydrous magnesium sulfate (50 g). The mixture stirred 3 h at room temperature then left to stand overnight. Filtered through dicalite and evaporated to dryness to give a pale yellow solid. This solid was stirred in dry ether (100 mL) for 30 min, then filtered, washed with ether, and dried in vacuo to give (S,E)-2-(2-bromobenzylideneamino)-2-phenylethanol (65.1 g) as a colourless solid.

MS (ES): m/z [M+H]$^+$ 304 and 306.

Compound 2

(S)-2-((S)-1-(2-Bromophenyl)but-3-enylamino)-2-phenylethanol

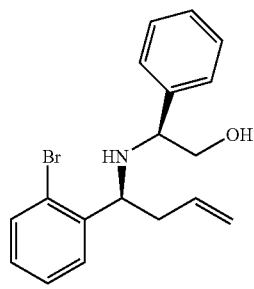

To a stirred suspension of zinc (70.8 mmol, 4.63 g, <10 micron) in tetrahydrofuran (35 mL) under nitrogen was added allyl bromide (70.8 mmol, 6.16 mL, 8.57 g) over 1 minute at room temperature. There was a moderate exotherm and the resultant grey suspension was stirred for 1.5 h then cooled in an ice/brine bath. A solution of (S,E)-2-(2-bromobenzylideneamino)-2-phenylethanol (compound 1; 23.60 mmol, 7.18 g) in tetra-hydrofuran (20 mL) was added dropwise over 30 minutes and stirred 10 minutes at 0° C. The bath was replaced with a 25° C. water bath and the grey suspension was stirred for 30 minutes at room temperature then quenched by addition of water, in one portion (50 mL). Methylene chloride (100 mL) was added and the mixture stirred for 1 h then to this mixture was added saturated sodium hydrogen carbonate (50 mL). The mixture was filtered through dicalite and layers separated. The separated aqueous layer was extracted further with methylene chloride and the organic extracts dried over sodium sulfate and evaporated to a pale yellow oil which was purified on 200 g silica pad using ethyl acetate/heptane (10-30%) to give pure (S)-2-((S)-1-(2-bromophenyl)but-3-enylamino)-2-phenylethanol (4.52 g), MS (ES): m/z [M+H]$^+$ 346 and 348.

Compound 3

(S)-1-(2-Bromophenyl)but-3-en-1-amine hydrochloride

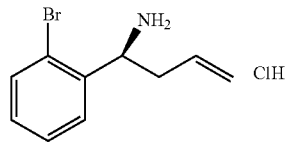

Method A

A stirred solution of (S)-2-((S)-1-(2-bromophenyl)but-3-enylamino)-2-phenyl-ethanol (compound 2; 124 mmol, 42.8 g) in methanol (500 mL) and methylamine (680 mmol, 71.1 mL, 33% solution in ethanol) was treated dropwise with a solution of periodic acid (340 mmol, 77 g) in methanol (50 mL) with ice/water cooling to maintain an internal temp less than 25° C. The mixture was stirred at room temperature for 3 hours then left to stand overnight. The mixture was quenched with 2M aqueous sodium hydroxide (300 mL) to give a thick precipitate that was stirred for 1 hr then the methanol was removed under vacuum. The mixture was filtered through dicalite and the gelatinous cake washed water (200 mL), then methylene chloride (250 mL) was added. Layers were separated and the aqueous layer extracted with methylene chloride (200 mL). Combined extracts dried over sodium sulfate and evaporated to give crude (S,E)-N-benzylidene-1-(2-bromo phenyl)but-3-en-1-amine (31.65 g) as a yellow oil.

A stirred solution of this crude product (15.37 mmol, 4.83 g) in tetrahydrofuran (80 mL) was treated with water (80 mL) to give a cloudy solution to which was added hydroxylamine hydrochloride (30.7 mmol, 2.14 g). After 45 min the tetrahydrofuran was removed under vacuum and the mixture acidified with 5M HCl (10 mL) and washed with ethyl acetate (2×50 mL) then basified with 10 M KOH and extracted with methylene chloride (3×50 mL). The combined organic layers were dried over sodium sulfate and evaporated to a pale yellow oil that was dissolved in ether, acidified with 2M HCl in ether, filtered and evaporated to give (S)-1-(2-bromophenyl)but-3-en-1-amine hydrochloride (3.16 g), MS (ES): m/z [M+H]$^+$ 226 and 228. Chiral HPLC and comparison with racemic material showed the material to be of 100% enantiomeric purity.

Method B

To a solution of (1R,3R,4S)-3-allyl-3-amino-1,7,7-trimethylbicyclo[2.2.1]heptan-2-one (241 mmol, 50 g) in 1,3-dichloropropane (400 mL) at ambient temperature under nitrogen was added 2-bromobenzaldehyde (253 mmol, 46.9 g) followed by D/L-camphorsulphonic acid (21.55 mmol, 5 g) and the solution was heated at heated to 50° C. overnight. A further 0.05 eq of 2-bromobenzaldehyde was added and the reaction stirred at 50° C. for a further 2 hours. To the reaction mixture at 50° C. was added a methanol solution of 0.5 M hydroxylamine acetic acid (1000 mL) [solution prepared by dissolving hydoxylamine hydrochloride (46.5 g) in methanol (500 mL)] followed by addition of sodium hydroxide pellets (20 g) allowing to stir for 30 min at ambient temperature and then slowly adding glacial acetic acid (30 g) at ambient temperature stirring for a further 30 min and then diluting to 1000 mL using methanol] and left to stir at 50° C. for 3 hours. The reaction mixture was cooled to 10° C. and slowly acidified with 10M hydrochloric acid (until pH 1 was attained). This was diluted with water (250 mL) and extracted with methylene chloride (4×500 mL), the acidic aqueous was then basified to pH 14 with sodium hydroxide pellets with ice-water cooling and then extracted with methylene chloride (3×500 mL), the combined organics were dried over sodium carbonate, filtered and evaporated to give a pale green oil which was loaded onto a silica pad (400 g silica), with methylene chloride and eluted with 100% ethyl acetate to 3% methanol (containing some 2M ammonia) in ethyl acetate to give (S)-1-(2-bromophenyl)but-3-en-1-amine (18.4 g) in an enantiomeric ratio of 97.6:2.4 determined by chiral HPLC, MS (ES); m/z [M=H]$^+$ 26 and 228. This material was converted to the hydrochloride salt with HCl in ether.

Compound 4

(S)-tert-Butyl 1-(2-bromophenyl)but-3-enylcarbamate

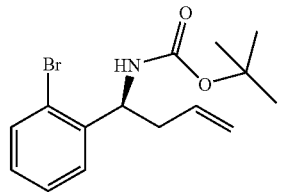

(S)-1-(2-Bromophenyl)but-3-en-1-amine hydrochloride (compound 3; 70.2 mmol, 18.44 g) was suspended in dry methylene chloride (200 mL) at ambient temperature and triethylamine (154 mmol, 21.49 mL) was added followed by di-tert-butyl dicarbonate (77 mmol, 16.86 g). The reaction mixture was diluted with methylene chloride (200 mL) and the resulting solution left to stir for two days at under argon.

The reaction mixture was quenched with 0.5% citric acid (200 mL) and extracted with methylene chloride (2×200 mL) the combined organic layers were washed with water and dried over sodium sulfate, filtered and evaporated to give (S)-tert-butyl 1-(2-bromophenyl)but-3-enylcarbamate (22.2 g), MS (ES): [M+H]$^+$ 326 and 328.

Compound 5

(S)-tert-Butyl 1-(2-bromophenyl)-4-hydroxybutylcarbamate

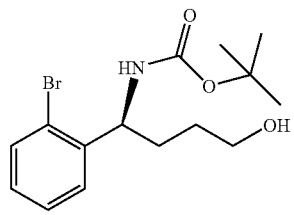

A solution of 2-methyl-2-butene (204 mmol, 21.68 mL) dissolved in tetrahydrofuran (150 mL) was cooled in a salt-ice bath and 1M boran-THF complex (34.1 mmol, 34.1 mL) was slowly added maintaining the temperature below 0° C. Upon complete addition the reaction mixture was left to stir for 10 minutes at 0° C. and then a tetrahydrofuran solution of (S)-tert-butyl 1-(2-bromophenyl)but-3-enylcarbamate (compound 4; 68.1 mmol, 22.23 g) was added slowly maintaining the temperature below 5° C. Once the addition was complete the cooling bath was removed and the temperature allowed to warm to room temperature and left to stir for 60 minutes. After 60 minutes the reaction mixture was cooled back to 0° C. and 4N sodium hydroxide (80 mmol, 20 mL) was slowly added at below 5° C. and this was followed by 27.5% aqueous hydrogen peroxide solution (68.1 mmol, 20 mL) keeping the temperature below 5° C., once the addition was complete the cooling bath was removed and the temperature allowed to warm to ambient temperature and left to stir overnight. The reaction mixture was diluted with ether (500 mL) then water (500 mL), the aqueous was phase separated and the aqueous re-extracted with ether (3×500 mL). The combined organic layers were dried over sodium sulfate, filtered and evaporated to give an white solid that was taken up in methylene chloride an loaded on to a silica pad and eluted with 40% ethyl acetate-heptane to give (S)-tert-butyl 1-(2-bromophenyl)-4-hydroxybutylcarbamate (8.08 g), MS (ES): m/z [M+H]+ 344 and 346.

Compound 6

(S)-4-(2-Bromophenyl)-4-(tert-butoxycarbonylamino)butyl methanesulfonate

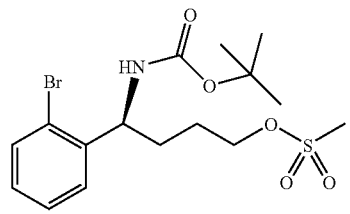

To a solution of (S)-tert-butyl 1-(2-bromophenyl)-4-hydroxybutylcarbamate (compound 5; 59.4 mmol, 20.44 g) in dry methylene chloride (500 mL) cooled in an ice bath was added N-ethyldiisopropylamine (119 mmol, 15.35 g) followed by the slow addition of methane sulfonyl chloride (60.0 mmol, 6.87 g) under nitrogen maintaining the reaction temperature below 5° C. Once the addition was complete the cooling bath was removed and the reaction mixture was allowed to warm to ambient temperature and left to stir for two days. The reaction mixture was evaporated at 45° C. under vacuum and residue taken up in methylene chloride (500 mL) washed with 0.5% citric acid, dried over magnesium sulfate with activated charcoal, filtered through a bed of dicalite and evaporated to give a slightly oily solid which was triturated with heptane to give (S)-4-(2-bromophenyl)-4-(tert-butoxycarbonylamino)butyl methanesulfonate 23.25 g) as a pale brown solid, MS (ES): m/z [M+H]+ 422 and 424.

Compound 7

(S)-2-(2-Bromophenyl)pyrrolidine hydrochloride

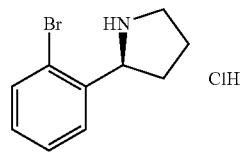

A 2M hydrogen chloride in ether solution (700 mL) in a 2 L-flask was cooled to 5° C. under nitrogen and (S)-4-(2-bromophenyl)-4-(tert-butoxycarbonylamino)butyl methanesulfonate (compound 6; 55.1 mmol, 23.25 g) dissolved in methanol (300 mL) was added slowly, maintaining the temperature below 20° C. A clear orange solution was formed which was left to stir at ambient temperature and monitored by thin layer chromatography (50% ethyl acetate-heptane) until no starting material was present. The excess HCl in ether was removed at 45° C. to give an orange/brown oil to which 2N HCl (200 mL) was added this was washed with ether (3×200 mL), cooled to less than 5° C., basified to pH 14 using solid KOH whilst maintaining the temperature below 10° C. with ice cooling. The aqueous mixture was extracted with methylene chloride (4×300 mL) and the combined organics were dried over sodium sulfate, filtered and evaporated to give a brown oil. This was dissolved in dry methanol (100 mL), cooled and 2N HCl in ether (150 mL) was slowly added maintaining the temperature below 10° C. The solvent was removed to give a slightly oily brown solid which was triturated with ether to give (S)-2-(2-bromophenyl)pyrrolidine hydrochloride (13.1 g), MS (ES): m/z [M+H]+ 226 and 228, as a pale brown solid. Chiral HPLC analysis demonstrated 100% enantiomeric purity.

Compound 8

5-(2-Bromophenyl)-3,4-dihydro-2H-pyrrole

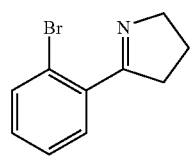

Sodium hydride (977 mmol, 23.45 g) was suspended in tetrahydrofuran (700 mL) and cooled to 5° C. with an ice-water bath. To this cold suspension was added 1-vinyl-pyrrolidin-2-one (465 mmol, 51.7 g) over approximately 20 minutes, maintaining an internal temperature reaction temp of less than 5° C. then ethyl 2-bromobenzoate (437 mmol, 100 g) was added. After the addition was complete the reaction was stirred at 5° C. for 10 minutes then refluxed for 2 hours and allowed to cool to room temperature. To the suspension was added 5N HCl (600 mL) dropwise, maintaining reaction temperature between 25° C. and 35° C. The bulk of the tetrahydrofuran was then distilled off at a temperature of 60° C. under vacuum. The resulting solution was cooled and further 5N hydrochloric acid (600 mL) was added and the mixture was refluxed overnight. The solution was then cooled with a salt-ice bath to 5° C. and basified by the careful addition of sodium hydroxide pellets (~250 g) maintaining an internal temperature between 10 and 15° C. When reaction mixture was at pH 13, the cooling bath was removed and temperature allowed to reach room temperature. The reaction was then extracted with methylene chloride (1 L) and the aqueous layer was extracted with further methylene chloride (2×1 L). The combined methylene chloride extracts were dried with sodium sulfate, filtered and evaporated to dryness to give 5-(2-bromophenyl)-3,4-dihydro-2H-pyrrole (92.2 g).

Compound 9

5-(2-Bromo-5-methylphenyl)-3,4-dihydro-2H-pyrrole

This compound was prepared in a similar manner as compound 8 starting from ethyl 2-bromo-5-methylbenzoate.

Compound 10

2(2-Bromophenyl)pyrrolidine

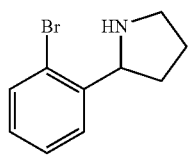

5-(2-Bromophenyl)-3,4-dihydro-2H-pyrrole (compound 8; 393 mmol, 88 g) was dissolved in methanol (1300 mL), then the acetic acid (330 mL) was added and the solution cooled to −65° C. under a nitrogen atmosphere. Sodium borohydride (589 mmol, 22.28 g) was added portionwise over 1 hour. The reaction was stirred at −65° C. for 30 minutes, then the cooling bath was removed and the reaction mixture temperature was allowed to rise to room temperature. The bulk of the methanol was removed under vacuum then 5N HCl (950 mL) was added and the solution extracted with ether (2×500 mL). The aqueous solution was then basified with sodium hydroxide pellets (310 g) with ice-bath cooling, maintaining the reaction temperature less than 30° C. The basified aqueous was then extracted with ethyl acetate (3×800 mL), the combined organics washed with brine (800 mL), dried with sodium sulfate, evaporated and chromatographed on 1 Kg of silica gel eluting with 19:1 to 9:1 methylene chloride-ethanol to give 2-(2-bromophenyl)pyrrolidine (68.5 g).

Compound 11

2-(2-Bromo-5-methylphenyl)pyrrolidine

This compound was prepared in a similar manner as compound 10 starting from Compound 9.

Compound 12

(E)-N-(2-Bromobenzylidene)-1,1-diphenylmethanamine

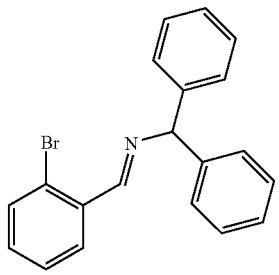

This material was prepared from diphenylmethanamine and 2-bromobenzaldehyde using the methods described by G. Cainelli et al, *J. Org. Chem.*, 1996, 51, 5134.

In a similar manner was prepared:

Compound 13

(E)-N-(2-Bromo-5-fluorobenzylidene)-1,1-diphenylmethanamine, starting from 2-bromo-5-fluorobenzaldehyde.

Compound 14

(E)-N-(2-Bromo-4-fluorobenzylidene)-1,1-diphenylmethanamine, starting from 2-bromo-4-fluorobenzaldehyde.

Compound 15

2-(2-Bromo-5-fluorophenyl)pyrrolidine

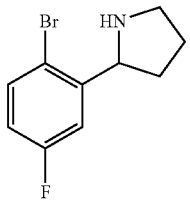

Compound 13 (13.58 mmol, 5 g) was dissolved in tetrahydrofuran under nitrogen and cooled to −78° C. A solution of 1M potassium tert-butoxide in tetrahydrofuran (16.29 mmol, 16.29 mL) was added dropwise resulting in a deep purple solution. After 5 minutes 1-chloro-3-iodopropane (136 mmol, 27.8 g) was added rapidly resulting in change of colour from purple to pink. The reaction was then warmed to 0° C. and stirred for 20 min until the colour had again changed to milky white. The reaction was quenched with water and extracted with methylene chloride, dried over sodium sulfate and concentrated under reduced pressure to give a liquid. The crude intermediate was dissolved in acetone and 2M hydrochloric acid (20 mL) added. The reaction was stirred overnight at room temperature then the acetone was removed under reduced pressure, reaction basified with 4M aqueous sodium hydroxide and extracted with methylene chloride, dried over sodium sulfate and concentrated under reduced pressure to give a dark red liquid that was dissolved in methanol, treated with 10M KOH and stirred at room temperature for 2 hours, extracted with methylene chloride, washed with water, dried over sodium sulfate and concentrated under reduced pressure. The product was purified by column chromatography on silica 2% methanol in methylene chloride to give 2-(2-bromo-5-fluorophenyl)pyrrolidine (1.7 g) as a brown liquid.

In a similar manner was prepared the following:

Compound 16

2-(2-Bromo-4-fluorophenyl)pyrrolidine, starting from Compound 14.

Compound 17

6-(2-Bromophenyl)-5-azaspiro[2.4]heptane

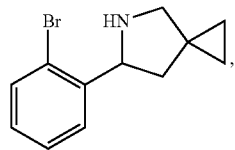

starting from Compound 12 and 1,1-bis(iodomethyl)cyclopropane.

Compound 18 tert-Butyl 2-(2-bromophenyl)pyrrolidine-1-carboxylate

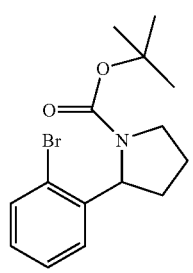

To a solution of 2-(2-bromophenyl)pyrrolidine (compound 10; 257 mmol, 58 g) in dry tetrahydrofuran (870 mL), cooled with a water bath, was added di-tert-butyl dicarbonate (264 mmol, 57.7 g) in tetrahydrofuran (150 mL) dropwise over ~30 minutes. The cooling bath was removed and the reaction stirred at room temperature for two days. The solvent was removed in vacuo and the residue taken up in methylene chloride (1 L), washed with 0.5M Citric acid (400 mL), brine (500 mL) and dried over sodium sulfate. Crystallisation from iso-hexane gave tert-butyl 2-(2-bromophenyl)pyrrolidine-1-carboxylate (42 g) and further tert-butyl 2-(2-bromophenyl)pyrrolidine-1-carboxylate (33 g) was obtained by chromatography of the mother liquors on 800 g silica gel, eluting with heptane-ethyl acetate 9:1 to 3:1.

In a similar manner was prepared the following:

Compound 19

(S)-tert-Butyl-2-(2-bromophenyl)pyrrolidine-1-carboxylate, starting from (S)-2-(2-bromophenyl)pyrrolidine Compound 20

(R)-tert-Butyl-2-(2-bromophenyl)pyrrolidine-1-carboxylate, starting from (R)-2-(2-bromophenyl)pyrrolidine Compound 22 tert-Butyl 2-(2-bromo-5-fluorophenyl)pyrrolidine-1-carboxylate, starting from 2-(2-bromo-5-fluorophenyl)pyrrolidine Compound 23 tert-Butyl 2-(2-bromo-5-methylphenyl)pyrrolidine-1-carboxylate, starting from 2-(2-bromo-5-methylphenyl)pyrrolidine Compound 24 tert-Butyl 2-(2-bromo-4-fluorophenyl)pyrrolidine-1-carboxylate, starting from 2-(2-bromo-4-fluorophenyl)pyrrolidine Compound 25 tert-Butyl 6-(2-bromophenyl)-5-azaspiro[2.4]heptane-5-carboxylate, starting from 6-(2-bromophenyl)-5-azaspiro[2.4]heptane.

Compound 26

(S)-tert-Butyl 2-(2-(5,5-dimethyl-1,3,2-dioxaborinan-2-yl)phenyl)pyrrolidine-1-carboxylate

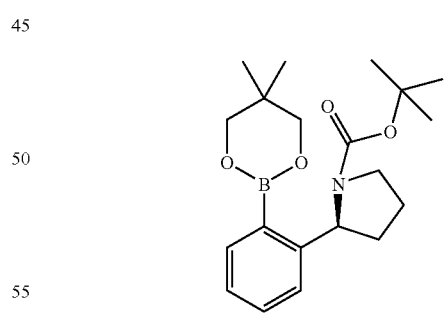

To a solution of Compound 19 (6.13 mmol, 2 g), 5,5,5',5'-tetramethyl-2,2'-bi(1,3,2-dioxaborinane) (9.20 mmol, 2.08 g), potassium acetate (18.39 mmol, 1.802 g) and 1,1'-bis(diphenylphosphino)ferrocenedichloropalladium (II) (6.13 mmol, 100 mg) placed into a pre-oven dried flask to which DMSO (20 mL) was added and heated to 110° C. under argon overnight. The reaction mixture was quenched into water (200 mL) and extracted with ethyl acetate (3×100 mL), the combined organics were washed with brine, dried over magnesium sulphate, filtered and evaporated to give a dark brown oil that was purified on a 120 g silica column, eluting with 20% ethyl acetate-heptane to give the title compound (1.08 g).

In a similar manner was prepared the following:

Compound 27 tert-Butyl 2-(2-(5,5-dimethyl-1,3,2-dioxaborinan-2-yl)phenyl)pyrrolidine-1-carboxylate, starting from Compound 18.

Compound 28

(R)-tert-Butyl 2-(2-(5,5-dimethyl-1,3,2-dioxaborinan-2-yl)phenyl)pyrrolidine-1-carboxylate, starting from Compound 20.

Compound 29 tert-Butyl 2-(2-(5,5-dimethyl-1,3,2-dioxaborinan-2-yl)2-bromo-5-fluorophenyl)pyrrolidine-1-carboxylate, starting from Compound 22.

Compound 30 tert-Butyl 2-(2-(5,5-dimethyl-1,3,2-dioxaborinan-2-yl)2-bromo-5-methylphenyl)pyrrolidine-1-carboxylate, starting from Compound 23.

Compound 31 tert-Butyl 2-(2-(5,5-dimethyl-1,3,2-dioxaborinan-2-yl)2-bromo-4-fluorophenyl)pyrrolidine-1-carboxylate, starting from Compound 24.

Compound 32 tert-Butyl 6-(2-((5,5-dimethyl-1,3,2-dioxaborinan-2-yl)methyl)phenyl)-5-azaspiro[2.4]heptane-5-carboxylate, starting from Compound 25.

Example 1

2-(2-((S)-pyrrolidin-2-yl)phenyl)-3-(trifluoromethyl)pyridine

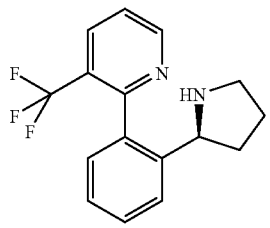

To a solution of 2-bromo-3-(trifluoromethyl)pyridine (2.212 mmol, 0.5 g) and compound 26 in toluene (60 mL) and ethanol (50 mL) was added 2M sodium carbonate solution (40 mmol, 20 mL) and tetrakis(triphenylphosphine)Pd(0) (0.087 mmol, 0.1 g). The solution was heated to reflux overnight. A solution of 4N sodium hydroxide solution was added and the mixture extracted with ethyl acetate. The organic layer was dried over magnesium sulphate, filtered and evaporated to give a brown oil that was purified on a 120 g silica column, eluting with 25% ethyl acetate-heptane to give (2S)-tert-butyl 2-(2-(3-(trifluoromethyl)pyridin-2-yl)phenyl)pyrrolidine-1-carboxylate (0.59 g). This material was dissolved in dry dichloromethane (3 mL) to which and trifluoroacetic acid (1.5 mL) was added and the solution left to stir until no starting material was evident by TLC. The reaction mixture was loaded onto a pre-conditioned 20 g SCX column and eluted with methanol, followed by ammonia/methanol. The appropriate fractions were evaporated to give (374 mg), that was isolated as both the maleate and succinate salts, MS (ES): m/z 293 [M+H]$^+$.

(2-((S)-Pyrrolidin-2-yl)phenyl)-3-(trifluoromethyl) pyridine was also isolated by separation of racemic (2-(pyrrolidin-2-yl)phenyl)-3-(trifluoromethyl) pyridine by supercritical fluid chromatography (SFC) using a Berger Multigram II SFC instrument at a flow rate of 40 mL/min, detector wavelength of 220 nm, a temperature of 35° C. and a pressure of 100 Bar CO2 on Chiralpak ADH column (25 cm×2 cm) with 20% Isopropanol/0.1% Isopropylamine as modifier.

In a similar manner were prepared the following:

Example 2

2-(2-((R)-Pyrrolidin-2-yl)phenyl)-3-(trifluoromethyl) pyridine

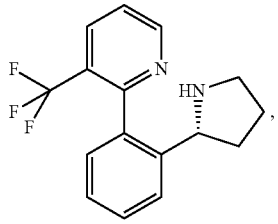

from Compound 28, MS (ES): m/z 293 [M+H]$^+$.

Example 3

2-(5-Fluoro-2-(pyrrolidin-2-yl)phenyl)-3-(trifluoromethyl)pyridine

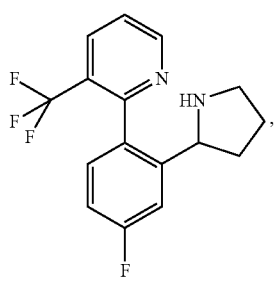

from Compound 29 and using 1,2-dimethoxyethane as solvent and microwave irradiation, MS (ES): m/z 311 [M+H]$^+$.

Example 4

6-(2-(3-(Trifluoromethyl)pyridin-2-yl)phenyl)-5-azaspiro[2.4]heptane

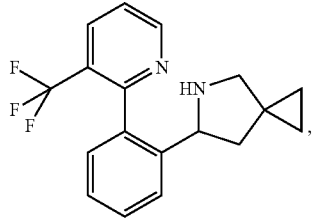

starting from Compound 32, MS (ES): m/z 319 [M+H]$^+$.

Example 5

2-(5-Methyl-2-(pyrrolidin-2-yl)phenyl)-3-(trifluoromethyl)pyridine

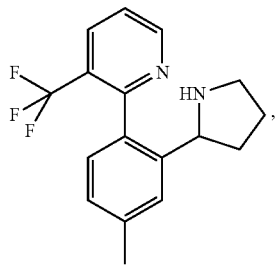

from Compound 30, MS (ES): m/z 307 [M+H]$^+$.

Example 6

2-(2-(Pyrrolidin-2-yl)phenyl)-3-methylpyridine

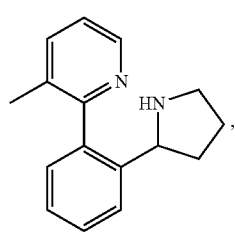

starting from Compound 27 and 2-bromo-3-methylpyridine, MS (ES): m/z 239 [M+H]$^+$.

Example 7

2-(4-Fluoro-2-(pyrrolidin-2-yl)phenyl)-3-methylpyridine

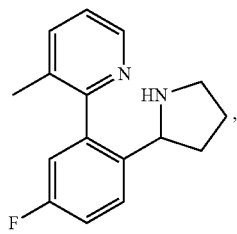

from Compound 31 and 2-bromo-3-methylpyridine and using 1,2-dimethoxyethane as solvent and microwave irradiation, MS (ES): m/z 257 [M+H]$^+$.

Example 8

2-(5-Fluoro-2-(pyrrolidin-2-yl)phenyl)-3-methylpyridine

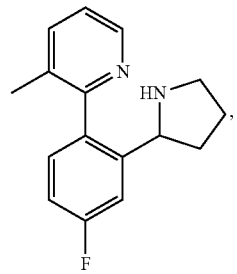

from Compound 29 and 2-bromo-3-methylpyridine and using 1,2-dimethoxyethane as solvent and microwave irradiation, MS (ES): m/z 257 [M+H]$^+$.

Example 9

2-(2-(Pyrrolidin-2-yl)phenyl)-3-methoxypyridine

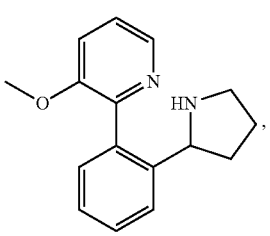

starting from Compound 27 and 2-bromo-3-methoxypyridine and using 1,2-dimethoxyethane as solvent and microwave irradiation, MS (ES): m/z 255 [M+H]+.

Example 10

2-(4-Fluoro-2-(pyrrolidin-2-yl)phenyl)-3-methoxypyridine

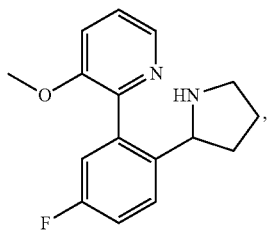

from Compound 31 and 2-bromo-3-methoxypyridine and using 1,2-dimethoxyethane as solvent and microwave irradiation, MS (ES): m/z 273 [M+H]+.

Example 11

2-(5-Fluoro-2-(pyrrolidin-2-yl)phenyl)-3-methoxypyridine

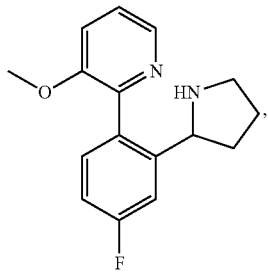

from Compound 29 and 2-bromo-3-methoxypyridine, MS (ES): m/z 273 [M+H]+.

Example 12

Biological Testing Using Automated Patch Clamp Electrophysiology

A: Cell Culture

HEK-hHCN1-2H10 cells were cultured in 225 cm$^2$ flasks, in MEM (with Earle's salts) supplemented with 10% Fetal-clone II+0.1 mM non essential amino acids+1 mM sodium pyruvate+10 mM HEPES+0.5 mg/mL G418. The cells were routinely maintained at 37° C. in an atmosphere of 5% $CO_2$ and 100% relative humidity until 50% confluent. 24 hours before use, cells were incubated at 30° C. to increase HCN1 membrane expression and harvested immediately prior to patch clamp experiments. The growth medium was aspirated under vacuum and the cells are washed in 50 mL Dulbecco's Phosphate Buffered Saline (without $CaCl_2$ and $MgCl_2$; D-PBS). The cells are then dissociated by incubating with 5 mL of a 1:1 mixture of 0.1% Trypsin/0.04% EDTA and cell dissociation buffer (CDS), at 37° C. for 2 minutes. Cell dissociation was terminated by the addition of 5 mL growth medium after which, the cells were mechanically dissociated by gently triturating 3-4 times using a 10 mL pipette. The cells were counted using a haemocytometer, recovered by centrifugation at 212 g for 1½ minutes and resuspended in 5 mLs of filtered external recording solution (see below). The cells were re-covered again by centrifugation as above and resuspended in filtered extracellular solution at a density of 2×10$^6$ cells per mL, triturating 4-5 times. The cells were transferred immediately to IonWorks.

B: Patch Clamp Recordings

Automated patch clamp recordings were performed using the IonWorks Quattro (MDS Analytical Technologies). The IonWorks Quattro was primed with intracellular (in mM: KGluconate, 130; NaCl, 10; $MgCl_2$, 1; EGTA, 1; HEPES, 10, pH 7.35) and extracellular solution (in mM: NaGluconate, 104; NaCl, 10; KCl, 30; $MgCl_2$, 1; $CaCl_2$, 1.8; Hepes, 10; glucose, 5; pH 7.35) recording solutions. Perforated patch clamp recordings were established with 0.1 mg/mL amphotericin B (in 0.36% DMSO) and the cells voltage clamped at −40 mV. Whole cell perforated patch clamp recordings were performed in two separate runs, with voltage steps to −80 mV and −120 mV for 1 s; leak subtraction was performed using a −10 mV voltage pulse prior to channel activation. Compounds were tested at 12 concentrations (half log intervals; 1% DMSO) and incubated for 10 minutes between current recordings. Cells were excluded with whole cell currents less 100 pS, seal resistances <50 MΩ or if the seal resistance varied by >50% during the course of the experiment. The amplitude of the time-dependent currents mediated by HCN, both pre- and post compound addition, was measured as the difference between the current recorded immediately after the capacity transient on stepping to the test voltage and the current measured after it had reached a steady state amplitude. Data were processed using the IonWorks Quattro System Software version 2 and analysed in Activity Base with XLFit 4.1, using a standard 4 parameter logistic function. Concentration response curves were generated and compound potency at the hHCN1 channel reported as the $pEC_{50}$, with the appropriate confidence intervals.

Compounds of the invention have a $pEC_{50}$ activity of greater than 4 at the −80 mV voltage step and preferred compounds of the invention have a $pEC_{50}$ activity greater than 5 at the −80 mV voltage step.

The invention claimed is:

1. A (pyrrolidin-2-yl)phenyl derivative having the general Formula I

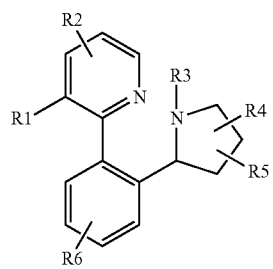

wherein
 $R_1$ is $(C_{1-4})$alkyl, halo$(C_{1-4})$alkyl, $(C_{1-4})$alkyloxy, or halo$(C_{1-4})$alkyloxy;
 $R_2$ is H, $(C_{1-4})$alkyl, halo$(C_{1-4})$alkyl, $(C_{1-4})$alkyloxy, halo$(C_{1-4})$alkyloxy or halogen;
 $R_3$ is H, $(C_{1-4})$alkyl or halo$(C_{1-4})$alkyl;

$R_4$ is H, $(C_{1-4})$alkyl or halo$(C_{1-4})$alkyl;
$R_5$ is H, $(C_{1-4})$alkyl or halo$(C_{1-4})$alkyl; or
$R_4$ and $R_5$, when bonded to the same carbon atom, can together with the carbon atom form a spiro$(C_{3-6})$cycloalkyl group, optionally substituted with halogen;
$R_6$ is H, $(C_{1-4})$alkyl, halo$(C_{1-4})$alkyl, $(C_{1-4})$alkyloxy, halo$(C_{1-4})$alkyloxy or halogen; or a pharmaceutically acceptable salt thereof.

2. The (pyrrolidin-2-yl)phenyl derivative of claim 1, wherein $R_1$ is halo$(C_{1-4})$alkyl.

3. The (pyrrolidin-2-yl)phenyl derivative of claim 1, wherein $R_2$, $R_3$, $R_4$ and $R_5$ are H.

4. The (pyrrolidin-2-yl)phenyl derivative of claim 3, wherein $R_6$ is H or F.

5. The (pyrrolidin-2-yl)phenyl derivative of claim 1, wherein the stereochemistry is that of the S-stereoisomer.

6. The (pyrrolidin-2-yl)phenyl derivative of claim 1 which is selected from:
2-(2-((S)-pyrrolidin-2-yl)phenyl)-3-(trifluoromethyl)pyridine;
2-(2-((R)-pyrrolidin-2-yl)phenyl)-3-(trifluoromethyl)pyridine;
2-(5-fluoro-2-(pyrrolidin-2-yl)phenyl)-3-(trifluoromethyl)pyridine;
6-(2-(3-(trifluoromethyl)pyridin-2-yl)phenyl)-5-azaspiro[2.4]heptane;
2-(5-methyl-2-(pyrrolidin-2-yl)phenyl)-3-(trifluoromethyl)pyridine;
2-(2-(pyrrolidin-2-yl)phenyl)-3-methylpyridine;
2-(4-fluoro-2-(pyrrolidin-2-yl)phenyl)-3-methylpyridine;
2-(5-fluoro-2-(pyrrolidin-2-yl)phenyl)-3-methylpyridine;
2-(2-(pyrrolidin-2-yl)phenyl)-3-methoxypyridine;
2-(4-fluoro-2-(pyrrolidin-2-yl)phenyl)-3-methoxypyridine;
2-(5-fluoro-2-(pyrrolidin-2-yl)phenyl)-3-methoxypyridine; or
a pharmaceutically acceptable salt thereof.

7. A pharmaceutical composition comprising a (pyrrolidin-2-yl)phenyl derivative of claim 1 or a pharmaceutically acceptable salt thereof in admixture with one or more pharmaceutically acceptable auxiliaries.

8. A pharmaceutical composition comprising a (pyrrolidin-2-yl)phenyl derivative of claim 6 or a pharmaceutically acceptable salt thereof in admixture with one or more pharmaceutically acceptable auxiliaries.

9. A method of treatment of pain which is mediated through modulation of the Ih channel, the method comprising administering to a patient in need thereof a therapeutically effective amount of a (pyrrolidin-2-yl)phenyl derivative of claim 1 or a pharmaceutically acceptable salt thereof.

10. The method of claim 9, wherein the pain is selected from the group consisting of neuropathic pain or inflammatory pain.

11. A method of treatment of pain which is mediated through modulation of the Ih channel, the method comprising administering to a patient in need thereof a therapeutically effective amount of a (pyrrolidin-2-yl)phenyl derivative of claim 6 or a pharmaceutically acceptable salt thereof.

12. The method of claim 11, wherein the pain is selected from the group consisting of neuropathic pain or inflammatory pain.

13. The (pyrrolidin-2-yl)phenyl derivative of claim 6 which is -2-(2-((S)-pyrrolidin-2-yl)phenyl)-3-(trifluoromethyl) pyridine or a pharmaceutically acceptable salt thereof.

14. The (pyrrolidin-2-yl)phenyl derivative of claim 6 which is -2-(2-((R)-pyrrolidin-2-yl)phenyl)-3-(trifluoromethyl) pyridine or a pharmaceutically acceptable salt thereof.

15. The (pyrrolidin-2-yl)phenyl derivative of claim 6 which is -2-(5-fluoro-2-(pyrrolidin-2-yl)phenyl)-3-(trifluoromethyl) pyridine or a pharmaceutically acceptable salt thereof.

16. The (pyrrolidin-2-yl)phenyl derivative of claim 6 which is -6-(2-(3-(trifluoromethyl)pyridin-2-yl)phenyl)-5-azaspiro[2.4]heptane or a pharmaceutically acceptable salt thereof.

17. The (pyrrolidin-2-yl)phenyl derivative of claim 6 which is -2-(5-methyl-2-(pyrrolidin-2-yl)phenyl)-3-(trifluoromethyl) pyridine or a pharmaceutically acceptable salt thereof.

18. The (pyrrolidin-2-yl)phenyl derivative of claim 6 which is -2-(2-(pyrrolidin-2-yl)phenyl)-3-methylpyridine or a pharmaceutically acceptable salt thereof.

19. The (pyrrolidin-2-yl)phenyl derivative of claim 6 which is -2-(4-fluoro-2-(pyrrolidin-2-yl)phenyl)-3-methylpyridine or a pharmaceutically acceptable salt thereof.

20. The (pyrrolidin-2-yl)phenyl derivative of claim 6 which is -2-(5-fluoro-2-(pyrrolidin-2-yl)phenyl)-3-methylpyridine or a pharmaceutically acceptable salt thereof.

21. The (pyrrolidin-2-yl)phenyl derivative of claim 6 which is -2-(2-(pyrrolidin-2-yl)phenyl)-3-methoxypyridine or a pharmaceutically acceptable salt thereof.

22. The (pyrrolidin-2-yl)phenyl derivative of claim 6 which is -2-(4-fluoro-2-(pyrrolidin-2-yl)phenyl)-3-methoxypyridine or a pharmaceutically acceptable salt thereof.

23. The (pyrrolidin-2-yl)phenyl derivative of claim 6 which is -2-(5-fluoro-2-(pyrrolidin-2-yl)phenyl)-3-methoxypyridine or a pharmaceutically acceptable salt thereof.

\* \* \* \* \*